United States Patent [19]

Melanson et al.

[11] Patent Number: 5,800,373

[45] Date of Patent: Sep. 1, 1998

[54] INITIATOR PRIMING FOR IMPROVED ADHERENCE OF GELS TO SUBSTRATES

[75] Inventors: David A. Melanson, Hudson, N.H.; Amarpreet S. Sawhney, Lexington, Mass.; Marc Alan Levine, Sharon, Mass.; John C. Spiridigliozzi, Dedham, Mass.; Thomas S. Bromander, Andover, Mass.

[73] Assignee: Focal, Inc., Lexington, Mass.

[21] Appl. No.: 410,037

[22] Filed: Mar. 23, 1995

[51] Int. Cl.$^6$ ................................................ A61F 13/00
[52] U.S. Cl. ........................ 602/52; 602/900; 602/904; 602/58; 604/20; 424/444; 424/426; 424/78.02
[58] Field of Search ................................ 427/2.24, 22.5, 427/2.3; 424/422, 426, 443–445; 602/41, 42, 52, 58, 900, 904, 78.02–78.07; 604/19.2

[56] References Cited

U.S. PATENT DOCUMENTS

| | | | |
|---|---|---|---|
| 3,552,986 | 1/1971 | Bassemir et al. | 117/12 |
| 3,939,049 | 2/1976 | Ratner et al. | 204/159.13 |
| 4,179,304 | 12/1979 | Rossomando | 106/177 |
| 4,511,478 | 4/1985 | Nowinski et al. | 210/691 |
| 4,741,872 | 5/1988 | De Luca et al. | 264/4.7 |
| 4,826,945 | 5/1989 | Cohn et al. | 528/76 |
| 4,938,763 | 7/1990 | Dunn et al. | 604/891.1 |
| 4,997,722 | 3/1991 | Adler | 428/596 |
| 5,100,992 | 3/1992 | Cohn et al. | 528/26 |
| 5,137,800 | 8/1992 | Neckers et al. | 430/281 |
| 5,160,745 | 11/1992 | De Luca et al. | 424/487 |
| 5,209,776 | 5/1993 | Bass et al. | 106/124 |
| 5,372,585 | 12/1994 | Tiefenbrun et al. | 604/59 |
| 5,385,606 | 1/1995 | Kowanko | 106/124 |
| 5,403,626 | 4/1995 | Kim et al. | 427/519 |
| 5,410,016 | 4/1995 | Hubbell et al. | 528/354 |

FOREIGN PATENT DOCUMENTS

| | | | |
|---|---|---|---|
| 0 635 276 A1 | 1/1995 | European Pat. Off. | A61L 25/00 |
| WO 93/16687 | 9/1993 | WIPO | A61K 9/50 |
| WO 93/17669 | 9/1993 | WIPO | A61K 9/50 |

OTHER PUBLICATIONS

Dumanian, et al., "A New Photopolymerizable Blood Vessel Glue that Seals Human Vessel Anastomoses Without Augmenting Thrombogenicity," *Plastic and Reconstructive Surgery* 95:901 (1995).

Kobayashi, et al., "Water-curable and biodegradable prepolymers," *J. Biom. Mat. Res.* 25:1481–1494 (1991).

Sawhney et al., "Optimization of photopolymerized bioerodible hydrogel properties for adhesion prevention," *J. Biomed. Mats. Res.*

*Primary Examiner*—Michael Powell Buiz
*Assistant Examiner*—Chalin Smith
*Attorney, Agent, or Firm*—Arnall Golden & Gregory, LLP

[57] ABSTRACT

An improved barrier or drug delivery system which is highly adherent to the surface to which it is applied is disclosed, along with methods for making for making the barrier. In the preferred embodiment, tissue is stained with a photoinitiator, then the polymer solution or gel having added thereto a defined amount of the same or a different photoinitator is applied to the tissue. On exposure to light, the resulting system polymerizes at the surface, giving excellent adherence, and also forms a gel in the rest of the applied volume. Thus a gel barrier of arbitrary thickness can be applied to a surface while maintaining high adherence at the interface. This process is referred to herein as "priming". The polymerizable barrier materials are highly useful for sealing tissue surfaces and junctions against leaks of fluids. In another embodiment, "priming" can be used to reliably adhere preformed barriers to tissue or other surfaces, or to adhere tissue surfaces to each other. A first surface and a barrier, or another surface, are prestained with initiator, and a thin layer of gellable monomer containing initiator is placed between them. Strong adhesion is obtained between the two surfaces on gelation of the monomer. In a similar fashion, tissue surfaces can be adhered to each other in repair of wounds and formation of anastomoses.

12 Claims, 1 Drawing Sheet

INITIATOR PRIMING FOR IMPROVED ADHERENCE OF GELS TO SUBSTRATES

BACKGROUND OF THE INVENTION

The present invention relates to methods and compositions for improving the adherence of polymer gels to surfaces, especially tissue surfaces; devices for applying the compositions and gels; and general methods for sealing surfaces with gels for therapeutic benefit.

Locally polymerized gels have been used as barriers and drug delivery devices for several medical conditions. Adherence of the formed gel to the tissue can be a problem, especially under surgical conditions, where the tissue surface to be treated is typically wet, and may further be covered with blood, mucus or other secretions. Hubbell and co-workers have described two methods for photopolymerizing gels in contact with tissue surfaces. In U.S. Ser. No. 08/022,687, hereby incorporated by reference, application of biodegradable macromers to tissue, followed by photopolymerization to form a gel, is described. Two methods for photopolymerizing gels are described. In "bulk" polymerization, a suitable photoinitiator and accessory reagents are solubilized or dispersed in a solution of gelling macromers. On application of light, the entire solution volume crosslinks to form a gel which acts as a local barrier or drug depot. These gels have substantial adherence to most surfaces, including tissue surfaces which are merely moist. However, if a confounding layer of fluid is present on the surface when the macromer/initiator solution is applied, then the gel may delaminate from the surface after its formation.

As also described in U.S. Ser. No. 08/024,657, which is hereby incorporated by reference, is an alternative way of form a gel layer on a surface, called the "interfacial" method. In this method, the surface to be coated is treated with a photoinitiator which adsorbs or absorbs to the surface. After washing away excess, unabsorbed photoinitiator, a polymerizable macromer solution is applied to the surface. On exposure to light, polymerization is initiated at the surface, and progresses outward into the solution to the limit of diffusion of the photoinitiator-generated radicals during their lifespan. Coating thicknesses of up to about 500 micrometers (microns) are routinely obtained. Since they are in effect "grown" from the tissue surface, such gel layers have excellent adhesion to the tissue surface under difficult conditions, including the presence of thin layers of fluid adherent to the surface. The limited thickness of such interfacial gels is desirable in some circumstances, but represents a major limitation where gels of substantially greater thickness than 500 microns are required, for example, for use in drug delivery, or in forming an effective barrier between the tissue surface and its surroundings.

In addition to the photopolymerizable gels described by Hubbell et al (WO93/17669) and Sawhney et al, (*J. Biomed. Mats. Res.* 28, 831–838, 1994), systems for forming drug delivery depots or barriers on surfaces include the polymers described in U.S. Pat. No. 4,938,763 to Dunn, et al., U.S. Pat. Nos. 5,100,992 and 4,826,945 to Cohn et al, U.S. Pat. Nos. 4,741,872 and 5,160,745 to De Luca et al, and U.S. Pat. No. 4,511,478 to Nowinski et al. Use of preformed barrier materials such as Goretex™ (W. L. Gore) has been described in the literature.

All of these materials are suitable for application to tissue and other substrates, although adhesion is in many cases limited, or in the case of the preformed barrier materials, essentially non-existant.

It is therefore an object of the present invention to provide methods and compositions for enhancing the adhesion of polymeric materials to tissue surfaces and other substrates.

It is a further object of the present invention to provide methods and compositions for increasing the thicknesses of polymeric materials which can be "tethered" to a tissue surface or other substrates.

SUMMARY OF THE INVENTION

An improved barrier, coating or drug delivery system which is highly adherent to the surface to which it is applied is disclosed, along with methods for making the barrier. In the preferred embodiment, tissue is stained with a photoinitiator, then the polymer solution or gel having added thereto a defined amount of the same or a different photoinitator is applied to the tissue. On exposure to light, the resulting system polymerizes at the surface, giving excellent adherence, and also forms a gel throughout the applied volume. Thus a gel barrier or coating of arbitrary thickness can be applied to a surface while maintaining high adherence at the interface. This process is referred to herein as "priming". The polymerizable barrier materials are highly useful for sealing tissue surfaces and junctions against leaks of fluids. In the present examples, the fluid is air; however, the principle is also applicable to other fluids, including blood, bowel contents, urine, and other fluids whose migration within a living organism must be contained.

In another embodiment, "priming" can be used to reliably adhere preformed barriers or coatings to tissue or other surfaces, or to adhere tissue surfaces to each other. A first surface and a performed barrier or coating, or another surface, are prestained with initiator, and a thin layer of polymerizable monomer containing initiator is placed between them. Strong adhesion is obtained between the two surfaces on polymerization of the monomer. In a similar fashion, tissue surfaces can be adhered to each other in repair of wounds and formation of anastomoses.

The priming method is suitable for any mode of polymerization. While especially effective in photopolymerization, chemical or thermal polymerization can also be accomplished by this method.

BRIEF DESCRIPTION OF THE DRAWINGS

FIGS. 1a and 1b are schematic drawings of a two-fluid-one-dispenser version, in which FIG. 1a is a longitudinal schematic cross-section and FIG. 1b is a view from the proximal end of the device.

DETAILED DESCRIPTION OF THE INVENTION

Figures 1A, 1B:
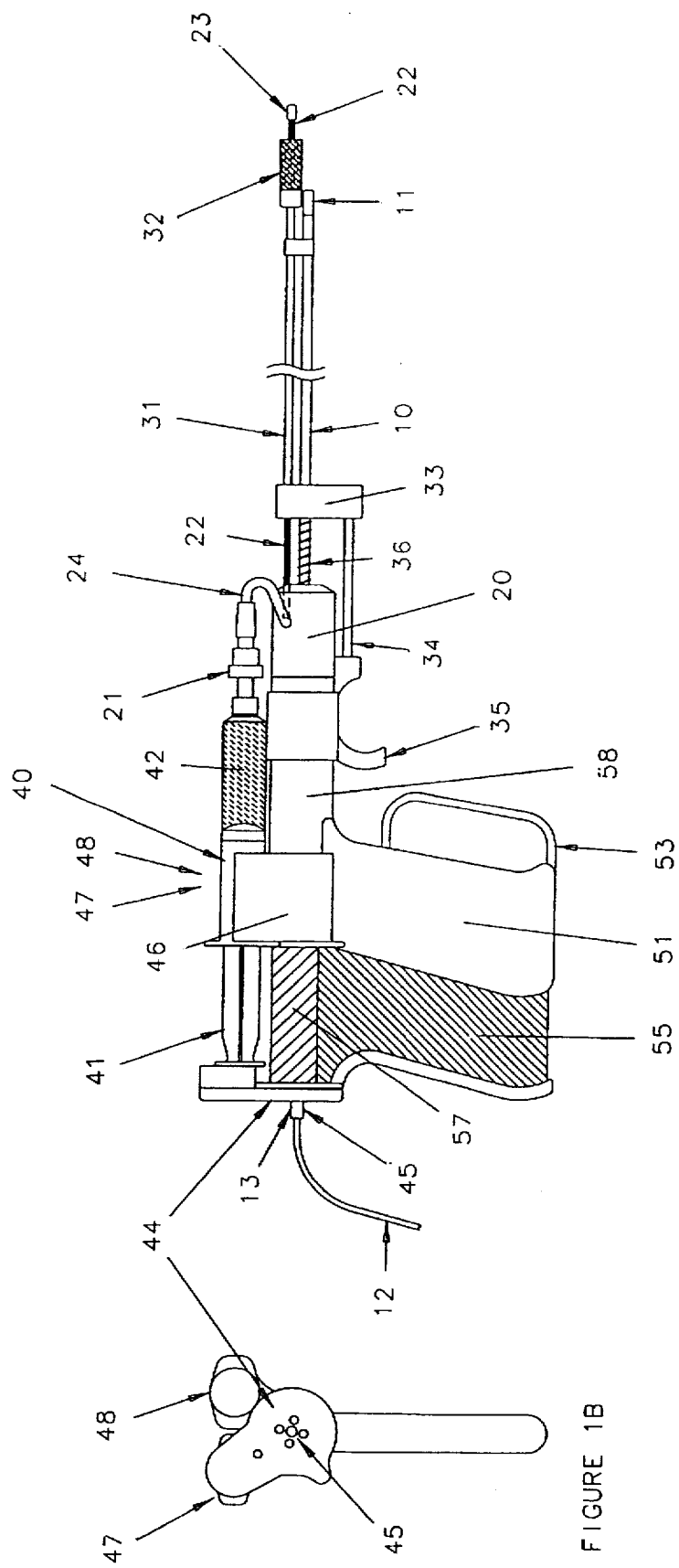

As described herein, one or more initiators are applied to a surface to form an absorbed layer. "Absorbed" is used herein to encompass both "absorbed" and "adsorbed". A solution of polymerizable molecules, referred to herein as "monomers", is then applied.

Methods

There are several embodiments of the method described herein.

In its simplest embodiment, initiator is applied directly to the surface, and the unabsorbed excess is optionally removed by washing or blotting. Then a liquid containing polymerizable monomers in combination with a photoinitator, which may be the same as or different from that absorbed in the first step, but which plays a similar role in the polymerization reaction, is applied.

The priming and monomer-application steps can also be combined. For example, if excess initiator is not removed before monomer addition, then subsequent application of monomer will result in mixture of initiator into the monomer layer. Similarly, if the monomer layer contains an initiator with a high affinity for the surface, then it is possible to apply a monomer layer containing initiator, and wait an appropriate time to allow preferential absorption of the initiator to the surface, to achieve the same effect.

All of these methods may collectively be described as application of the monomer in an "initiator-incorporating manner", encompassing any means of application and mixing which results in both an absorbed layer of initiator, and a layer of monomer incorporating an initiator, being present on a surface to be coated.

Compositions

MONOMERS

Any monomer capable of being polymerized to form a surface coating can be used. The monomers may be small molecules, such as acrylic acid or vinyl acetate; or they may be larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, U.S. Pat. Nos. 4,741,872 and 5,160,745 to De Luca et al., or U.S. Ser. No. 08/022,687 by Hubbell et al. Properties of the monomer, other than polymerizability, will be selected according to the use, using principles as known in the art. There is an extensive literature on the formulation of polymerizable coating materials for particular applications; these formulae can readily be adapted to use the improved adherence-promoting polymerization system described herein with little experimentation.

In the particular application area of coating of tissues, cells, medical devices, and capsules, formation of implants for drug delivery or as mechanical barriers or supports, and other biologically related uses, the general requirement of the coating materials are biocompatibility and lack of toxicity. For all biologically-related uses, toxicity must be low or absent in the finished state for externally coated non-living materials, and at all stages for internally-applied materials. Biocompatibility, in the context of biologically-related uses, is the absence of stimulation of a severe, long-lived or escalating biological response to an implant or coating, and is distinguished from a mild, transient inflammation which accompanies implantation of essentially all foreign objects into a living organism.

The monomer solutions should not contain harmful or toxic solvents. Preferably, the monomers are substantially soluble in water to allow their application in a physiologically-compatible solution, such as buffered isotonic saline. Water-soluble coatings may form thin films, but more preferably form three-dimensional gels of controlled thickness.

It is especially preferable in cases involving implants that the coating formed be biodegradable, so that it does not have to be retrieved from the body. Biodegradability, in this context, is the predictable disintegration of an implant into small molecules which will be metabolized or excreted, under the conditions normally present in a living tissue.

A preferred monomer is the photopolymerizable, biodegradable, water-soluble macromers described by Hubbell et al in U.S. Ser. No. 08/022,687. These monomers are characterized by having at least two polymerizable groups, separated by at least one degradable region. When polymerized at concentrations above about 5% in water, they form coherent gels which persist until eliminated by self-degradation. In the most preferred embodiment, the macromer is formed with a core of a polymer which is not adherent to tissue, such as the polyalkylene oxide polyethylene glycol, flanked by hydroxy acids such as lactic acid, having coupled thereto acrylate groups. Preferred monomers, in addition to being biodegradable, biocompatible, and non-toxic, will also be at least somewhat elastic after polymerization or curing. Elasticity, or stretchability, is often exhibited by polymers with low modulus. Brittle polymers, including those formed by polymerization of cyanoacrylates, are not generally effective in contact with biological soft tissue.

We find that monomers with longer distances between crosslinks are generally softer, more compliant, and more elastic. Thus, in the polymers of Hubbell, et al., increased length of the water-soluble segment, such as polyethylene glycol, tends to give more elastic gel, and these tend to adhere better, especially under stretching (as when applied to lung). Molecular weights in the range of 10,000 to 35,000 (of polyethylene glycol) are preferred for such applications, although ranges from 3,000 to 100,000 are useful.

INITIATORS

The term "initiator" is used herein in a broad sense, in that it is a composition which under appropriate conditions will result in the polymerization of a monomer. Compounds for initiation may be photoinitiators, chemical initiators, thermal initiators, photosensitizers, co-catalysts, chain transfer agents, and radical transfer agents. All initiators known in the art are potentially suitable for the practice of the priming technique. The critical property of an initiator is that the polymerization will not proceed at a useful rate without the presence of the initiator.

The "priming" initiator must adhere sufficiently to the surface to be coated to provide a local source of initiation of the reaction with the particular monomers to be applied. The initiator must also not be toxic when used in biologically-related applications. The initiator is preferably a photoinitiator. In discussing photoinitiators, a distinction may be drawn between photosensitizers and photoinitiators—the former absorb radiation efficiently, but do not catalyze polymerization well unless the excitation is transferred to an effective initiator or carrier. Photoinitiators as referred to herein include both photosensitizers and photoinitiators, unless otherwise noted.

Photoinitiation is an important curing mechanisms for addition polymerization, and especially for curing of vinylic and acrylic-based monomers. Any of the photoinitiators found in the art may be suitable, if they adhere to the particular surface. Examples of photo-oxidizable and photo-reducible dyes that may be used to initiate polymerization include acridine dyes, for example, acriblarine; thiazine dyes, for example, thionine; xanthine dyes, for example, rose Bengal; and phenazine dyes, for example, methylene blue. Other initiators include camphorquinones and acetophenone derivatives.

The choice of the photoinitiator is largely dependent on the photopolymerizable regions. For example, when the macromer includes at least one carbon-carbon double bond, light absorption by the dye causes the dye to assume a triplet state, the triplet state subsequently reacts with the amine to form a free radical which initiates polymerization. Preferred dyes for use with these materials include eosin dye and initiators such as 2,2-dimethyl-2-phenylacetophenone, 2-methoxy-2-phenylacetophenone, and camphorquinone. Using such initiators, copolymers may be polymerized in situ by long wavelength ultraviolet light or by light of about 514 nm, for example.

A preferred photoinitiator for biological use is Eosin Y, which absorbs strongly to most tissue and is an efficient photoinitiator.

Thermal polymerization initiator systems may also be used. Systems that are unstable at 37° C. and initiate free radical polymerization at physiological temperatures include, for example, potassium persulfate, with or without tetramethyl ethylenediamine; benzoyl peroxide, with or without triethanolamine; and ammonium persulfate with sodium bisulfite.

It is known in the art of photopolymerization to use a wavelength of light which is appropriate for the activation of a particular initiator. Light sources of particular wavelengths or bands are well-known.

CO-INITIATORS AND COMONOMERS

Any of the compounds typically used in the art as radical generators or co-initiators in photoinitiation may be used. These include co-catalyst or co-initiators such as amines, for example, triethanolamine, as well as other trialkyl amines and trialkylol amines; sulfur compounds; heterocycles, for example, imidazole; enolates; organometallics; and other compounds, such as N-phenyl glycine.

Co-monomers can also be used. They are especially useful when the monomer is a macromolecule, as in Example 1 below; in that case, any of the smaller acrylate, vinyl or allyl compounds can be used. Comonomers can also act as accelerators of the reaction, by their greater mobility, or by stabilizing radicals. Of particular interest are N-vinyl compounds, including N-vinyl pyrrolidone, N-vinyl acetamide, N-vinyl imidazole, N-vinyl caprolactam, and N-vinyl formamide.

SURFACTANTS, STABILIZER, AND PLASTICIZERS

Other compounds can be added to the initiator and/or monomer solutions. Surfactants may be included to stabilize any of the materials, either during storage or in a form reconstituted for application. Similarly, stabilizers which prevent premature polymerization may be included; typically, these are quinones or hindered phenols. Plasticizers may be included to control the mechanical properties of the final coatings. These are also well-known in the art, and include small molecules such as glycols and glycerol, and macromolecules such as polyethylene glycol.

DRUGS

Biologically active materials may be included in any of the coatings described herein, as ancillaries to a medical treatment (for example, antibiotics) or as the primary objective of a treatment (for example, a gene to be locally delivered). A variety of biologically active materials may be included, including passively-functioning materials such as hyaluronic acid, as well as active agents such as growth hormones. All of the common chemical classes of such agents are included: proteins (including enzymes, growth factors, hormones and antibodies), peptides, organic synthetic molecules, inorganic compounds, natural extracts, nucleic acids, lipids and steroids, carbohydrates, glycoproteins, and combinations thereof.

SURFACES TO BE TREATED

Surfaces to be coated include biologically-related surfaces of all kinds. In particular, any tissue or cell surface is contemplated, as well as the surface of a device to be used in the body or in contact with bodily fluids. A coating may be applied to the surface of any of these, in an amount effective to improve tenacity of adherence. Moreover, the technique may be used to adhere surfaces to each other. For example, wounds in living tissue may be bonded or sealed using this technique or preformed medical appliances may be bonded to tissue.

The priming technique can also be used on non-tissue surfaces in general, where useful bonds may be formed between similar or dissimilar substances, and solid or gel coatings are tightly adhered to surfaces. In particular, a pre-formed gel, or other fragile material, may be tightly adhered to a supporting material by this method.

Methods of Treatment

Generally, any medical condition which requires a coating or sealing layer may be treated by the methods described herein to produce a coating with better adherence. In the examples below, lung tissue is sealed against air leakage after surgery using the priming technique. Likewise, wounds may be closed; leakage of blood, serum, urine, cerebrospinal fluid, air, mucas, tears, bowel contents or other bodily fluids may be stopped or minimized; barriers may be applied to prevent post-surgical adhesions, including those of the pelvis and abdomen, pericardium, spinal cord and dura, tendon and tendon sheath. The technique may also be useful for treating exposed skin, in the repair or healing of incisions, abrasions, burns, inflammation, and other conditions requiring application of a coating to the outer surfaces of the body. The technique is also useful for applying coatings to other body surfaces, such as the interior of hollow organs, including blood vessels.

GENERAL SEALING OF BIOLOGICAL TISSUES

As shown in the examples below, the priming method of polymerization is especially effective in the sealing of biological tissues to prevent leakage. However, the examples also demonstrate that a degree of sealing can be achieved with photopolymerizable systems without the improvement of priming the tissue with photopolymerizing initiator. There have been numerous attempts to reliably seal tissue with a number of materials, including most prominently cyanoacrylates and fibrin glues. None of these prior art techniques has been entirely satisfactory. Cyanoacrylates, which polymerize on exposure to moisture, and can be accelerated by amines, are very "stiff" once polymerized. If there is any motion of the biological material, they tend to crack, and lose their self-cohesion and/or their adherence to tissue. Fibrin glues can be difficult to prepare, especially in the currently-preferred autologous version; they require enzymatic or toxic chemical means to be gelled or crosslinked; and they are rapidly degraded by native enzymes.

APPLICATION TECHNIQUES AND DEVICES

Both priming and polymer addition may be accomplished by simple dripping of material onto the surface to be coated. This can be accomplished using common devices such as a syringe, a pipet, or a hose, depending on scale. More uniform applications may be obtained using an applicator, such as a brush, a pad, a sponge, a cloth, or a spreading device such as a finger, a coating blade, a balloon, or a skimming device. These may further be used to rub the surface to improve penetration of the primer or the monomer, or to mix primer and monomer in situ on the surface. In large-scale applications, fluid layers may be applied with large-scale coating machinery, including roll coaters, curtain coaters, gravure and reverse gravure devices, and any of the coating devices known in the art. Sprayers may be used at any scale, especially for lower-viscosity primers or polymerizable monomer layers.

Application techniques and devices may be combined, as in applying fluid from a syringe, and then rubbing it into the surface with a finger tip. Such operations may be repeated, as in applying drops of priming initiator; rubbing these into the surface with a brush; repeating this operation; adding monomer solution; rubbing it in; and finally applying additional layers of monomer before or during the application of curing means, such as light, heat, or slow release of peroxide radicals.

An additional application means which is required in many coating techniques of the invention, and in particular in the preferred coating method which uses photoinitiation to cure the monomer, is a light source. For large-scale application, flood lamps and similar devices are useful. In small, localized applications, such as tissue sealing and coating, it may be preferable to use a localized source such as a fiber optic or light guide, which can project radiation of the appropriate wavelength onto the site to be treated to cause polymerization of the monomer. Also, a light emitter could be carried on a device, as a miniature bulb. A focused beam from a remote source could be suitable if, for example, the surface was exposed. In exposed surfaces, it is possible that ambient light could be sufficient to polymerize the coating, especially at high initiator levels.

Each of the applications means can be separate, so that a kit of application means could contain one or more reservoirs, one or more pads or brushes, and if required at least one light guide. The application means could also be combined in whole or in part. For example, a dripping device, such as a tube, could be combined with a spreading device, such as a brush. These could further be combined with a light guide. Such combination devices are especially desirable in treatment of living organisms, and especially humans, to maximize the simplicity of a procedure and the probability of correctly conducting it.

Thus, a combination device for conducting a primed photopolymerization in a biological or medical setting will contain at least the following elements:

a) one or more means for applying a fluid to a surface, selected from dripping means, irrigating means, spraying means, applicator pad means including brushes, balloons, fabrics and foams, and rigid surfaces, such as spatulas, for applying paste-like or highly viscous fluids;

b) one or more optional means for spreading or rubbing a fluid onto a surface, which may be brushes, pads, rigid or semi-rigid protuberances, and which may be the same or different as the fluid-application means;

c) one or more reservoirs, or connecting conduits for receiving the contents of reservoirs into the device, for a primer, a monomer solution, and/or a combination thereof;

d) light-delivery means, which may be a fiber optic, a light guide, a focused remote beam, or a locally-deployed light source, such as a miniature lamp;

e) a proximal end adapted to be held by the person administering the treatment, optionally further including means for selection among the one or more application means, spreading means, reservoir means, and light-delivery means (i.e., switching means); and f) a distal end or ends, optionally adapted to be sterilizable, from which the one or more fluids are dispensed.

Other options for the device include metering means for the fluids, so that a controlled amount may be dispensed, or a controlled pressure may be maintained; feedback devices, such as optical viewers and indicators of function; and interlocks to correctly sequence the application procedure, or to insure dispensing of the required amounts of initiator, monomer, and light or other polymerization stimulator.

Many devices and arrangements can be constructed that meet these requirements. One embodiment of such a device is illustrated in FIGS. 1a and 1b, in which FIGS. 1a is a longitudinal schematic cross-section, and FIG. 1b is a view from the proximal end of a two-fluid-one-dispenser version.

In FIG. 1a, a main shaft (10), of which the distal end is shown, carries light from a remote light source (not shown) coupled into an optical fiber or fibers (12) passing into the shaft through a bushing or strain-relief member (13) at the proximal end of the device, and through the axis of the device to a distal emission element (11). The emission element contains appropriate optical elements to distribute the light onto the site where polymerization is to occur. These may be as simple as a window, but may include other arrangements known in the art to distribute the light, including diffusers, lenses or gratings, and collimating stops.

Syringes (47, 48) (see also FIG. 1b) with check valves (21) are provided for the delivery of fluids via a connector (24) through a bifurcation in the body extension (20) to a fluid delivery conduit (22), the ends of which are shown. The fluid delivery conduit may have a specialized applicator tip (23), such as a spray nozzle, or may be smooth for simple delivery of fluid by dripping. The fluid delivery conduit is optionally surrounded by a slidable tube (31) carrying a spreading device (32), which is connected by a block (33) which slides on the main shaft (10). The sliding block (33) slides the telescoping tube (31) on the fluid delivery conduit (22). The block is connected by a connecting rod (34) to a trigger mechanism (35), which is used to slide the spreading device (32) either distally of the emission element (23), or proximately of it, depending on the step of the priming operation. The trigger (35) may also optionally be provided with spring tensioners (36) or latches or detents for controlling position (not illustrated).

A syringe barrel (40) containing a fluid to be delivered (42) is fitted with a plunger (41). The plunger is selectively contactable by a plunger driver (44), which may be rotated about the device axis (45) to drive either of the two syringes (47, 48) shown in FIG. 1b. The syringes are held on the device by a clamp (46).

The plunger driver (44) is connected to a freely sliding rod (57) which can slide into a recess (58) in the device under the influence of slidable hand grip (55), which slides into handle (51). A finger guard (53) is provided for convenience.

In operation, the device is used as follows. With the spreading device 32 retracted to the proximal position, the plunger driver 44 is positioned over the filled initiator (primer) syringe 47, and by compressing the slidable portion of the hand grip 55 into the handle 51, fluid is dripped from delivery conduit 22 onto the target area. Then the spreading device is moved to the distal position and is used, by movement of the device as a whole by the operator, to spread the initiator priming solution over the entire target area. Alternatively, the spreading device may be in the distal position during primer delivery, so that the fluid is distributed by it.

Next, the spreading device is optionally retracted, and the driver (44) is moved to drive syringe 48, which contains a solution with monomer, initiator, carrier amine, and other ingredients. The monomer solution is dripped onto the target region, the spreader is advanced, and the monomer is rubbed into and distributed on the surface. Optionally, the spreader is retracted and further monomer is applied to the surface, optionally with the aid of the spreader, to form a thicker coat. Alternatively, the spreader may be in the distal position throughout delivery, so that the fluid is distributed by it.

Finally, the spreader is retracted, and the light source is activated to deliver light to emission element 11 to polymerize the coating on the surface of the tissue. Optionally, further monomer solution can be delivered during the emission of light to build up additional thickness. For this reason, both the delivery tube 22 and the main shaft 10 are preferably opaque to the light being used. This is conveniently achieved by constructing these elements of metal, such as standard syringe needle tubing. If the monomer solution is sensitive to room light, then the monomer syringe 48 should also be shielded or made of opaque material, and the monomer delivery path elements 21, 24 and 20 should likewise be opaque to the radiation wavelengths which initiate polymerization in the particular monomer/initiator combination. The rest of the device is made of any suitable material, such as a medical grade plastic. The device as a whole, or particular parts thereof such as the fluid dispensing pathway or the spreader, may be disposable.

In another embodiment, not illustrated, the elements 44, 55, 57 and 58 are omitted. The syringe plungers 41 are then exposed, and are driven directly by thumb pressure.

In an alternative embodiment, not illustrated, an additional trigger may be enclosed within guard 53 to connect to rachet means for delivering a controlled amount of fluid with each squeeze of the trigger. Suitable rachet means are known in the art; one such means is disclosed in co-pending application U.S. Pat. No. 08/036,128. In an alternative embodiment, separate fluid pathways may be provided for each of the two fluids. The separate pathways may be parallel or concentric. In the former case, separate spreading elements may be provided for each pathway.

PACKAGING

The materials for making the coating can be packaged in any convenient way, and may form a kit, alone or together with the application device. The reactive monomers are preferably stored separately from the initiator, unless they are co-lyophilized and stored in the dark, or otherwise maintained unreactive. A convenient way to package the materials is in three vials (or prefilled syringes), one of which contains concentrated initiator for priming, the second of which contains reconstitution fluid, and the third containing dry or lyophilized monomer. Dilute initiator is in the reconstitution fluid; stabilizers are in the monomer vial; and other ingredients may be in either vial, depending on chemical compatibility. If a drug is to be delivered in the coating, it may be in any of the vials, or in a separate container, depending on its stability and storage requirements.

It is also possible, for a more "manual" system, to package some or all of the chemical ingredients in pressurized spray cans for rapid delivery. If the monomer is of low enough viscosity, it can be delivered by this route. A kit might then contain a spray can of initiator; a spray can or dropper bottle of monomer, initiator and other ingredients; and an optional spreading or rubbing device. If the monomer and initiator system were designed to polymerize under the influence of natural or operating room light, possibly with the supplement of a chemical initiator or carrier such as a peroxygen compound, then the technique could be suitable for field hospital or veterinary situations.

EXAMPLES

Example 1.
Relative adhesion of coating to primed and unprimed surfaces.

Fresh pig lung was primed in one area with a solution of photoinitiator (Eosin Y, 1 mg/mL (1000 ppm in normal saline) and in another area with normal saline (prior art control). Excess fluid was removed by blotting. About 0.5 mL of monomer solution was applied to each spot. The monomer was polyethylene glycol (35,000 Daltons) terminated with caprolactone (average of 3.3 caprolactone groups per polyethylene glycol molecule) and capped with acrylic acid, essentially as described in Hubbell et al. The monomer solution contained 15% monomer (w/w), 90 mM triethanolamine, 20 ppm (w/w) Eosin Y, and 5 microliters/mL vinylpyrrolidine (v/v). The samples were irradiated with green light until cured (40 sec. at 100 mW/cm2) into a firm, transparent gel. Initial adherence was seen in both primed and control spots, although the primed spots had better overall adherence.

The lung was connected to a pressure-controlled inflation apparatus, and subjected to chronic fatigue for 1 hour at 25 to 30 cm of water pressure, in 6 second cycles. This was designed to simulate the effects of breathing. After the fatigue test, the primed gel spots were still adherent, but the control gel spots could easily be lifted from the lung surface with forceps. Thus, adhesion under chronic stress was better with priming before polymerization.

Example 2.
Sealing of wedge resection of lung

In lung operations, it is common to make a "wedge resection" to remove diseased areas. A combination stapler/cutter is used to simultaneously cut and staple along one side of the wedge to be removed, and is then used to staple and cut the other side so that a wedge-shaped piece of lung is removed, while the remaining lung is simultaneously stapled closed. Despite a high staple density, the staple lines are prone to leak air, which can produce severe complications in a patient undergoing such an operation.

Frozen-thawed pig lungs were wedge-resectioned, using a ProxiMate™ TLC 55 reloadable linear cutter/stapler (Ethicon; Somerville, N.J.). Every second staple was omitted from the outer staple lines in the cassette to reliably induce leaks. Lungs were inflated to a pressure of 40 cm $H_2O$, and leaks were observed by pushing the stapled area just under the surface of a water bath (similar to leak testing of an inner tube.) Next, staple lines were primed with 1000 ppm Eosin Y, blotted, and treated with the macromer mixture of Example 1 which was then cured as described.

In a standard test for durability, the lungs were inflated to 20 cm water pressure for 10 cycles, over a period of 1 minute, and then held for 30 seconds at 40 cm water. The primed and sealed lung sections showed no leaks, demonstrating the effectiveness of the priming system in sealing known leaks.

Finally, pressure was increased in the primed lungs to determine the maximum pressure before leakage. Small leaks were typically seen at 75 cm water or above.

Example 3.
Lap/Shear Strength of Primed and Unprimed Bonds.

Adhesion under shear of gel to rat skin was determined on an Instron™ apparatus using standard methods. The biological surface was rat back skin, freshly removed from euthanized animals. It was glued to a glass slide, and treated as described below. A casting chamber was positioned above the skin, which also contained a gauze mesh which protruded from the chamber. Monomer solution was injected into the chamber and polymerized. The chamber was removed, and the tensile strength of the bond was determined by shearing the lap between the glass slide and the gauze mesh in a standard load cell on the Instron.

Skin treatments included none (control); primed; primed and pre-coated with monomer solution by drip; and primed, pre-coated with monomer solution by drip, and rubbed or mixed with a brush. A monomer solution as in Example 1 was applied, except that the monomer, "8KL5", had a smaller PEG molecule (8000 D), and was extended with lactate groups rather than caprolactone groups. With unprimed skin, a different initiator, Irgacure™ 651 (Ciba Geigy), was also used in the gelling monomer mixture.

With the non-primed Irgacure® system, average load at failure for 6 to 8 samples ranged from 49 grams of force with low-intensity mixing of monomer onto the surface, to 84 to 274 g. with rubbing. Similar results were obtained with the Eosin catalysed system with no primer (146 g avg, range 80–220). When the tissue was pre-primed with Eosin, and monomer solution was thoroughly mixed with a brush, the failure force increased to 325 g (range 220–420). Thus priming can quantitatively improve early adherence, in addition to its much larger improvement in adherence after flexing.

Example 4.
Sealing of a bronchus

A bronchus was stapled and cut during lobectomy by the techniques described for wedge resectioning. The staple line was coated as described in Example 2, likewise preventing or stopping air leaks.

Example 5.
Sealing of a laceration

A laceration 2 mm deep by 2 cm long was made on an isolated lung with a scalpel; the scalpel was taped to control the depth of cut. The lung was tested and found to leak. The laceration was primed, filled with monomer solution containing initiator, and the monomer was photopolymerized. The leak was sealed by this procedure.

Example 6.
Coating of a medical device

A length of polyurethane tubing extrusion used for catheter shafts was dipped into an aqueous solution containing 20 ppm eosin. Excess eosin was rinsed off with water. The primed tubing was dipped into a solution containing 10% monomer (type 8KL5, as in Example 3), 90 mM triethanolamine, 5 ppm vinylpyrrolidone, and 20 ppm eosin. Excess monomer was allowed to drip off. The monomer layer on the tubing was then photopolymerized to form an adherent gel coating. The adherence was strong enough to survive sectioning of the tubing with a razor blade; photomicrography showed complete adherence of the gel to the tubing. As a prior art control, the shaft was not primed. After dipping the un-primed shaft into the same monomer solution, the coating on the shaft was photopolymerized. A gel was formed, but failed to adhere to the shaft, and fell off during handling.

Example 7.
Priming for surface adherence

Two surfaces of Pebax™ polyurethane were stained with 1000 ppm Eosin Y and rinsed. Polymerizable monomer solution (10% 8KL5 in water containing 20 ppm eosin) was placed between the surfaces, and the sandwich was exposed to green light. Gel formed in the interface and held the surfaces together. In a control experiment, in which the surfaces were not primed, polymerization of the monomer occurred but no significant adherence of the surfaces was found.

Example 8.
Priming of surfaces

On exposure to 1000 ppm of Eosin Y, surfaces of Teflon™ fluoropolymer and of polyethylene were observed to stain significantly. When monomer was added to such surfaces, and allowed to stand briefly, gels were formed on illumination. Adherence seemed inferior to that obtained on polyurethane.

Example 9.
Priming of Uterine Horn and Adherence of Gel Layers

A model system was established for placing of barriers on mammalian uteruses after operations. Freshly excised uterine horns from euthanized pigs were removed from a saline bath and treated with 1000 ppm Eosin. Controls were not primed. Polymerizable monomer solution as in Example 7 was applied to the primed and control areas. Adherence of gel layers to the primed areas was very firm, while gels on control areas could be dislodged.

We claim:

1. A process for reducing leakage of bodily fluids, including air, the process comprising:

priming an area of a tissue surface by applying a polymerization initiator to the area, and applying to the area a solution containing a biodegradable, biocompatible, polymerizable monomer in combination with an initiator; and polymerizing the monomer to seal the area and to reduce leakage of the bodily fluids through the area, whereby the polymerization occurs in both an interfacial and bulk manner.

2. The process of claim 1 wherein the area is first primed with one or more initiators, and then the monomer solution is applied to the area to result in mixing of the initiator with the monomer in the solution.

3. The process of claim 1 wherein the surface is the surface of dura.

4. The process of claim 1, in which the body fluid is selected from blood, serum, air, urine, bowl contents, cerebrospinal fluid, tears, and mucus.

5. The process of claim 4, in which the fluid is air.

6. The process of claim 1, wherein the tissue surface is part of the respiratory tract.

7. The process of claim 6, in which the surface is a surface of the lung.

8. The process of claim 1 further comprising applying a pharmaceutically active material to the area.

9. The process of claim 8 wherein the pharmaceutically active material is applied in combination with one or both of the initiator and the monomer solution.

10. The process of claim 1, in which the polymer is photopolymerizable and the initiator is a photoinitiator.

11. The process of claim 10, in which the photoinitiator is an eosin.

12. The process of claim 1 wherein the surface is the surface of dura.

* * * * *